United States Patent [19]
Roreger et al.

[11] Patent Number: 5,456,745
[45] Date of Patent: Oct. 10, 1995

[54] FLEXIBLE, HYDROPHILIC GEL FILM, THE PROCESS FOR ITS PRODUCTION AND THE USE OF IT

[75] Inventors: Michael Roreger; Fritz Herrmann; Hans-Rainer Hoffmann; Harald List, all of Neuwied, Germany

[73] Assignee: LTS Lohmann Therapie-Systeme GmbH & Co. KG, Neuwied, Germany

[21] Appl. No.: 392,813

[22] Filed: Aug. 11, 1989

[30] Foreign Application Priority Data

Aug. 13, 1988 [DE] Germany ............... 38 27 561.9

[51] Int. Cl.$^6$ ............... C09D 101/28; C09D 189/00
[52] U.S. Cl. ............... 106/128
[58] Field of Search ............... 106/128

[56] References Cited

U.S. PATENT DOCUMENTS

| | | | |
|---|---|---|---|
| 4,010,038 | 3/1977 | Iwasaki et al. | 106/128 |
| 4,394,452 | 7/1983 | Hash et al. | 106/128 |
| 4,655,840 | 4/1987 | Wittwer et al. | 106/128 |

OTHER PUBLICATIONS

Nikolaos A. Peppas, "Hydrogels in Medicine and Pharmacy", p. 122 no date availible.

*Primary Examiner*—David Brunsman
*Attorney, Agent, or Firm*—Sprung Horn Kramer & Woods

[57] ABSTRACT

A flexible, hydrophilic, water-swellable but insoluble gel film which consists of
(a) 0.5 to 30%-wt of at least one water-soluble polymer being anion-active at neutral pH
(b) 0.5 to 50%-wt of at least one water-soluble polymer being cation-active at neutral pH
(c) 0.1 to 20%-wt of at least one moisturizer
(d) 0.1 to 70%-wt of water
(e) 0 to 75%-wt of water-soluble or water-dispersible auxiliaries
(f) 0 to 50%-wt of active substance a process for its production and the use of this film for the production of a device creating interactions between the gel film and a solid, liquid, or gaseous substrate.

10 Claims, 2 Drawing Sheets

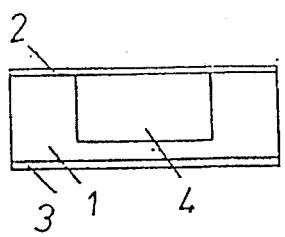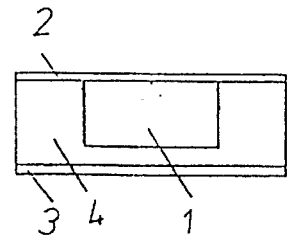
FIG. 7c  FIG. 7d
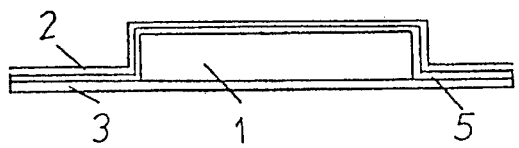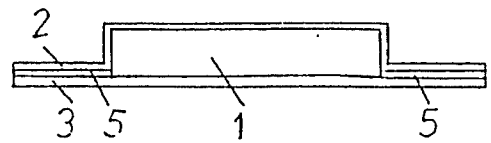
FIG. 8a  FIG. 8b
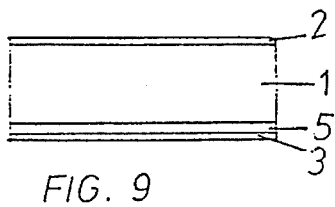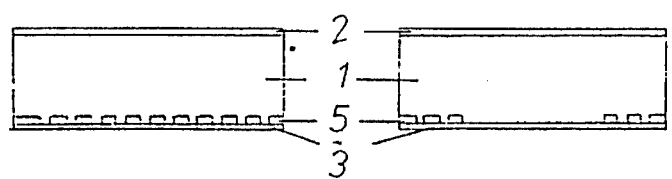
FIG. 9  FIG. 10a  FIG. 10b
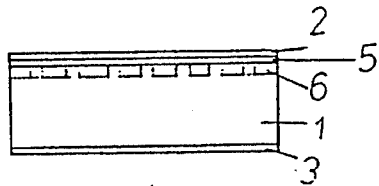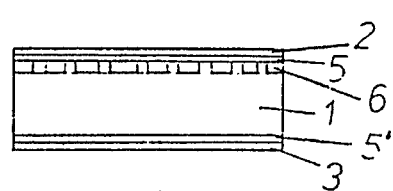
FIG. 11a  FIG. 11b
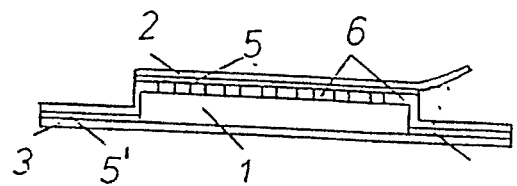
FIG. 12

FLEXIBLE, HYDROPHILIC GEL FILM, THE PROCESS FOR ITS PRODUCTION AND THE USE OF IT

The present invention relates to a flexible, hydrophilic, water-swellable, but insoluble gel film, to a process for its production and to the use of this film for the production of a device creating an interaction between the gel film and a solid, liquid, or gaseous substrate.

During the last years, hydrophilic films and film-like hydrogels have increasingly been used in the most diverse fields of pharmacy and medicine, e.g. as wound dressings, coverings for various medicals and substrates, as active substance carriers for the oral, buccal, rectal, vaginal, dermal or transdermal application of active substances, implants and artifical vessels (detailed list, see J. D. Andrade, Ed., Hydrogels for medical and related applications, 1976/N. A. Peppas, Ed., Hydrogels in Medicine and Pharmacy, Vol. I, II, III, 1987).

The main reason for the increasing interest in the use of hydrogels on intact and damaged skin or on the mucous membranes is that hydrogels in most cases exhibit a significantly better tolerance with biological surfaces and tissues than lower hydrophilic materials, especially if they are applied over a longer period of time.

For instance, water-swellable, hydrophilic films in general have a lower skin irritation potential after application to the skin than occlusive films or membranes which may cause skin irritations only because of the occlusive effect when used over long periods of time. Furthermore, the manufacture from aqueous solution or dispersion has clear advantages towards the manufacture from organic solution with regard to toxicology and environmental pollution.

Hydrogels are generally divided into heat reversible and irreversible gels. Irreversible hydrogels are gels in which a three-dimensional stable network of polymer chains having covalent and physical bonds is established by cross-linkage of monomers. These hydrogels are capable of swelling under absorption of water, however, they are no longer soluble in water, even if heated.

These hydrogels are particularly useful for the manufacture of stable gel films due to the cross-linking. In this connection, polymer films on the basis of various acrylic acid and methacrylic acid monomers have achieved the most important significance in medicine and pharmacy. These films have a high tear strength in swollen condition, however, the capability to swell is limited. For certain purposes those polymer films may be rendered self-adhesive by the addition of adequate auxiliaries, however, the adhesive effect is extremely reduced when contacting water or due to residual water in the film.

The disadvantage of the irreversible hydrogels is that their useability frequently is limited due to the toxicological properties of the monomers, or the cross-linking agents used, particulary when used on mucous membranes or damaged tissue.

Heat-reversible hydrogels are usually produced by dissolution of hydrophilic polymers in hot water and subsequent cooling, whereby the formation of gel starts upon cooling below the jellification point. These hydrogels are of lower mechanical stability, particularly upon contact with water. Molecules are dissolved from the gel, even if this happens very slowly, and the tear strength decreases with increasing swelling, whereby this effect is enhanced, e.g. when applied to the skin by the warming to body temperature. The advantage is that hydrogels may be manufactured by selection of suitable physiologically acceptable polymers and auxiliaries, which can be employed even on very damaged tissue or in body cavities. However, if these hydrogels are employed, films are frequently produced after application, e.g. after spreading or spraying, at the place of application itself. Thus an exact dosage of active substance in the case of hydrogels containing active substance is rendered impossible. Furthermore, the polymers establishing the structure and the polymer combinations used frequently limit the application to a certain and very narrow purpose.

Thus it was the task of the present invention to develop a hydrophilic, flexible gel film which, without the need to use cross-linking agents, exhibits a mechanical stability in swollen condition and has a high water absorption capacity, said stability enabling easy handling, and the gel film being produced of components having optimum skin and mucous membrane tolerance, and which may be loaded with active substance, if needed.

Surprisingly the solution of this task was found in a certain composition, i.e. the combination of (a) 0.5 to 30%-wt of at least one water-soluble polymer being anion-active at neutral pH (b) 0.5 to 50%-wt of at least one water-soluble polymer being cation-active at neutral pH (c) 0.1 to 20%-wt of at least one moisturizer and (d) 0.1 to 70%-wt of water In addition the gel film may contain (e) 0 to 75%-wt of water-soluble or water-dispersible auxiliaries and (f) 0 to 50%-wt of active substance Water-soluble polymers being anionic at neutral pH may be anionic cellulose derivatives, anionic starch derivatives, anionic galactomannan derivatives, anionic vegetable polysaccharides, anionic polyacrylates and polymethacrylates. Anionic cellulose derivatives are, e.g. sodium carboxymethyl cellulose, cellulose acetate phthalate, hydroxypropylmethylcellulose phthalate (HPMPC), methyl cellulose phthalate, carboxymethylethylcellulose, ethyl carboxyethyl cellulose, cellulose acetate succinate, methyl cellulose succinate, methyl cellulose phthalate succinate, or ethyl cellulose succinate. Anionic starch derivatives are, e.g. sodium carboxymethyl starch, or starch acetate phthalate; anionic galactomannans are, e.g. galactomannan phosphoric acid ester (Meyprofilm® of Meyhall), carboxymethyl guar (Meyprogum® of Meyhall), and carboxymethyl hydroxypropyl guar (Jaguar CMHP® of Meyhall); anionic vegetable polysaccharides are, e.g. pectins, carrageenanes, alginates, or xanthene (Keltrol®); anionic polyacrylates or polymethacrylates are, e.g. copolymers on the basis of methacrylic acid and methacrylic acid methylesters (Eudragit L/S® of Röhm-Pharma), or copolymers on the basis of acrylic acid, acrylic acid esters and methacrylic esters having free carboxyl groups (Aquakeep® of Itoh/Carboset® of Goodrich).

Water-soluble polymers being cationic at neutral pH may be type-A-gelatin, cationic galactomannan derivatives, such as, e.g. guar hydroxypropyl trimonium chloride (Jaguar C® of Meyhall), as well as cationic polyacrylates and polymethacrylates, such as, e.g. copolymers of dimethylaminoethyl methacrylate and neutral methacrylic acid (Eudragit E® of Röhm-Pharma), or copolymers of acrylic and methacrylic acid esters having a low content of quaternary ammonium groups (Eudragit RL/RS® of Röhm-Pharma). The gel film may contain as moisturizers, e.g. alcohol, such as glycerol, propylene glycol, sorbitol, or low molecular polyethylene glycols.

In the technical literature, one frequently finds the hint that the combination of certain anionc and cationic polymers in aqueous solution is not possible due incompatibility and agglomeration during the solution step due to the opposite charges of the polymers. For instance, when combining sodium carboxymethylcellulose and gelatin below their isoelectrical point which is in the case of type-A-gelatin at a pH of approximately 8.5 to 9.0, or when combining anionic, vegetable polysaccharides with type-A-gelatin (literature: 1) E. Doelker, "Water-swollen Cellulose Derivatives in Pharmacy", in N. A. Peppas, "Hydrogels in Medicine and Pharmacy", Vol II, CRC press 1987, page 122; 2) H. P. Fiedler, "Lexikon der Hilfsstoffe für Pharmazie, Kosmetik und angrenzende Gebiete", Editio Cantor Aulendorf 1981, p. 423).

The present invention provides a way to prevent these incompatibility reactions between anionic and cationic polymers during the dissolution process, by adding to the solvent, which is water, or a mixture of water and a water-miscible solvent, a volatile additive which prevents the reaction of polymers of different charge, and which has a boiling temperature between 25° C. and 120° C., preferably between 40° C. and 80° C. In this solution at least one water-soluble polymer being anion-active at neutral pH, at least one water-soluble polymer being cation-active at neutral pH, at least one moisturizer, and optionally other formulation components are dissolved, emulsified, or suspended, whereby the temperature of the solution during the dissolving process does not exceed the boiling temperature of the volatile additive. The mixture so obtained is cast into a mold, or spread onto a carried, and dried in known manner to a defined residual moisture, whereby by removing the volatile additive a flexible, hydrophilic gel film is formed which does swell in water but is non-soluble. The volatile additive which prevents the reaction of polymers having different charges preferably is of basic or acidic character.

The volatile additive effects that during the dissolving process one of the contrary polymer components is temporarily inactivated by reversible salt formation in such a way that its charge does not have any effect. By the removal of the volatile additive during drying, the salt formation is reversed and the polymer or the polymers are lead to its/their original form. The mechanical stability of the resulting gel film results from the attraction of the contrary charges of the basis polymers. Volatile additives having basic character, e.g. are ammonium hydroxide, or primary, secondary and tertiary amines having boiling points between 25° C. and 120° C., such as, e.g. isopropylamine, tertiary butylamine, diethylamine, isobutylamine, diisopropylamine, isoamylamine, or triethylamine.

Volatile additives having acidic character, e.g. are hydrochloric acid, carbonic acid, acetic acid, or formic acid.

Moisturizer and residual water content are responsible for the flexibility of the gel film. Thus the gel film must not be dried completely, since this would lead to the fact that the gel film would become brittle and flawy. The optimum content of residual water and moisturizer has to be determined for the individual gel film by way of tests and is also dependent, e.g. on the kind and amount of further auxiliaries and/or active substances which may be contained in the gel film.

The gel film may contain as water-soluble or water-dispersible auxiliaries, e.g. softeners, thickeners, penetrations accelerators, tackifiers, preserving agents, disinfectants, pH-regulators, antioxidants, emulsion stabilizers, cross-linking agents, fillers and/or foam stabilizers.

The gel film may contain as softeners citric acid esters, such as triethylcitrate or acetyl triethylcitrate; tartaric acid esters, such as dibutyltartrate; glycerol ester, such as glycerol diacetate or glycerol triacetate; phthalic acid esters, such as dibutyl phthalate or diethyl phthalate; and/or hydrophilic surfactants, preferably hydrophilic non-ionic surfactants, such as, e.g. partial fatty acid esters of sugars, polyethylene glycol fatty acid ester, polyethylene glycol fatty alcohol ether, or polyethylene glycol-sorbitan-fatty acid esters.

Thickeners, e.g. are natural substances and their derivatives, such as collagen, galactomannans, starches, starch derivatives and hydrolyzates, cellulose derivatives, such as methyl cellulose, hydroxypropylcellulose (HPC), hydroxyethyl cellulose, ethylhydroxyethyl cellulose or hydroxypropyl methyl cellulose, colloidal silicic acids, swell clays, sugars, such as lactose, saccharose, fructose or glucose, as well as synthetic substances, such as polyvinyl alcohol, polyvinyl pyrrolidone, vinylpyrrolidone-vinylacetate-co-polymers, polyethylene glycols, or polypropylene glycols. Collagen is the preferred thickening agent.

The gel film may contain as penetration accelerator, e.g. alkyl sulphates, alkyl sulphonates, alkali soaps, fatty acid salts of multivalent metals, betaine, amine oxides, fatty acid esters, mono-, di- or triglycerides, long-chain alcohols, sulphoxides, nicotinic acid esters, salicylic acid, N-methylpyrrolidone, 2-pyrrolidone, or urea.

The gel film may contain as tackifiers, e.g. natural resins or gums, such as mastic, damar, elemi, styrax, euphorbium, sandarac, galbanum, gum arabic, or karaya gum; modified natural resins, such as, e.g. colophony derivatives; or synthetic resins or gums, such as, e.g. polyacrylates, polymethacrylates, polyvinyl ether, polyurethane, polyisobutylene, polyvinylester, or silicones. In a special embodiment the gel film comprises as tackifier sugar, honey and/or panthenol.

The gel film may contain as preserving agents, e.g. p-Cl-m-cresol, phenylethyl alcohol, phenoxyethyl alcohol, chlorobutanol, 4-hydroxybenzoic acid methylester, 4-hydroxybenzoic acid propylester, benzalkonium chloride, cetylpyridinium chloride, chlorhexidine diacetate, or chlorhexidine digluconate, ethanol, or propylene glycol.

The gel film may contain as disinfectant halogens, such as polyvidone-iodine; halogen compounds, such as sodium hypochlorite or chloramine T; oxidants, such as hydrogen peroxide or potassium permanganate; aryl mercury compounds, such as phenylmercury borate or merbromin; alkyl mercury compounds, such as thiomersal; organotin compounds, such as tri-n-butyl-tin benzoate; silver protein compounds, such as silver protein actetyltannate; alcohols, such as ethanol, n-propanol or isopropanol; phenols, such as thymol, o-phenyl-phenol, 2-benzyl-4-chlorophenol, hexachlorophen or hexylresorcinol; or organic nitrogen compounds, such as 8-hydroxyquinoline, chlorquinaldol, clioquinol, ethacridine, hexetidine, chlorhexedine, or ambazone.

The gel film may contain as pH-regulators, e.g. glycine buffers, citrate buffers, borate buffers, phosphate buffers, or citric acid-phosphate-buffers.

The gel film may contain as anitoxidants, e.g. ascorbic acid, ascorbic palmitate, tocopherol acetate, gallic acid ester, butylhydroxyanisole, or butylated hydroxytoluene.

The gel film may contain as emulsion stabilizers nonionic emulsifiers, such as, e.g. higher fatty alcohols, partial fatty acid ester of multivalent alcohols, partial fatty acid esters of sugars, polyethylene glycol fatty acid ester, polyethylene glycol fatty alcohol ether, polyethylene glycol-sorbitane-fatty acid ester; but as well amphoteric emulsifiers, such as, e.g. phospholipides, ampholytic soaps, or proteins; cationic emulsifiers, such as, e.g. quaternary ammonium compounds or pyridinium compounds; and anionic emulsifiers, such as, e.g. fatty acid salts of multivalent metals, alkylsulphates, and alkyl sulphonates.

The gel film may contain as filling agents, e.g. micro crystalline cellulose, aluminum oxide, zinc oxide, titanium dioxide, talcum, silicon dioxide, magnesium silicate, magnesium-aluminium silicate, kaoline, hydrophobic starch, calcium stearate, or calcium phosphate.

The gel film may contain as cross-linking agent, e.g. multivalent cations of metals, such as zinc-, magnesium-, aluminum-, calcium-, chromium-, copper-, or iron-ions; or anions of multivalent acids, such as sulphate-, phosphate-, silicate-, borate-, tartrate-, or citrate-ions.

The gel film may have a lipophilic inner phase, whereby this lipophilic phase may be present in undivided and coherent form, or in divided form, preferably divided into small particles and drops. The lipophilic inner phase may consist, e.g. of natural, semi-synthetic or synthetic fats and oils, such as olive oil, castor oil, peanut oil, soy oil, linseed oil, sesame oil, jojoba oil, avocado oil, hydrogenates peanut oil, hydrogenated castor oil, triglyceride mixtures (Miglyol®, Softisan®); or silicone oils, natural, semi-synthetic, or synthetic waxes, such as beeswax, wool wax, earth wax, spermaceti wax, oleic acid oleyl ester, isopropyl palmitate, isopropyl myristate, ethyloleate, cetyl palmitate or cetyl stearate; fatty alcohols, such as dodecyl alcohol or cetyl alcohol; fatty acids, such as myristic acid, oleic acid or linoleic acid; propoxylated, ethoxylated or sulphated fatty alcohols; fatty acid alkylamides; fatty acid-protein-condensation products, phospholipides, sterols, or hydrocarbons, such as paraffins, or paraffin oils. If the lipophilic inner phase of the gel film is present in divided form, auxiliary agents for stabilization of the divided phase are added, such as, e.g. emulsifiers and/or protecting colloids.

In a particular embodiment the composition of the flexible hydrophilic gel film is chosen in such a way that the film is transparent.

During dissolving process of the formulation components, air may be mixed into the mass so that the gel film after spreading or casting exhibits a porous structure. The manufacture and stabilization of the porous structure may be supported, for example, by the addition of foamers, such as saponins, alginic esters, amine oxides, or fatty amine oxides.

The composition of the flexible, hydrophilic gel film may be chosen in such a way that the gel film is biological decomposable, whereby biological decomposition means, e.g. the action of UV-light, action of microbes, or the action of enzymes.

The flexible, hydrophilic gel film may have a multi-layer structure. For instance, at least two gel films may be connected to the composite according to known processes. It is possible too, to bring together one or more gel films with one ore more lipophilic polymer films to a composite of any desired structure. In this case, the individual layers of the composite can be connected with each other and be coherent, or they can be divided into segments which are surrounded or enclosed by the overlying or underlying layer. For instance, a lipophilic adhesive layer may be applied to a gel film continuously or divided in the form of points or rhombs, whereby the gel film can fill the spaces between the lipophilic segments. In another embodiment the gel film is combined with textile fabrics, non-wovens and/or natural or synthetic foams. In this multi-layer composite the individual layers can be manufactured according to known processes as separate pieces and then brought together. The layers may as well penetrate each other, for example in the case when the gel mass is applied to a fabric, non-woven, or a foam prior to the formation of the film, and the formation of the film takes place after absorption of the gel mass into the fabric or foam.

The flexible, hydrophilic gel film can be used in the production of devices for creating an interaction between the gel film and a solid, liquid or gaseous substrate. The interaction between gel film and substrate can be created by direct contact or indirect contact between gel film and substrate; in the case of indirect contact the interaction is created by parts of the device, such as, e.g. adhesive layers, control elements, or permeable separating elements. In order to prevent drying up or growing in of germs the gel film is provided with an impermeable back layer and on the opposite side with a detachable impermeable protective layer by known process (FIG. 1).

Back layer and protective layer preferably are foils, of polyamide, polycarbonate, polyester, polyethylene, polypropylene, polyvinyl chloride, polyvinyl ester, polyurethane, polystyrole, polytetrafluoroethylene, cellophane, cellulose acetate, aluminium; or they are composite foils made of the above mentioned materials. The gel film then, e.g. is divided into sections appropriate for the use and made-up. However, the division of the gel film can also be carried out by the user himself. For instance, the gel film is stored in rolled or folded condition in a container, and the applier may separate segments, e.g. by cutting, having a size adequate for the purpose. The area of the segments may also be predetermined by specified lines, e.g. by pre-punching or pre-cutting the gel film, so that the applier can tear off individual segments without having to use technical auxiliaries. Another method to divide the gel film is that prior to the production of the film the gel mass is cast into molds by which the size of the produced film is determined. In this case the appliance of an impermeable protective layer and/or impermeable back layer onto the gel film can be dispensed with, if the mold is part of the making-up and is sealed after the production of the film, e.g. by means of a sealing foil.

If the gel film is used to produce a device for creating interactions between the gel film and a solid substrate, or between the gel film and a liquid substrate of limited surface being surrounded by a solid substrate, this device for the creation of the contact between gel film and the substrate is provided with a securing element. This securing element may, e.g. be a band or bandage, a conventional adhesive plaster or an adhesive foil.

The fixation or securing on the substrate may as well be performed by the gel film itself, provided that it contains tackifiers, or, if it is multi-layered, at least parts of the contact layer exhibit adhesive properties towards the substrate (FIG. 9, 10). A further possibility to fix or secure the device is that the back layer is of larger dimension than the gel film segment and that at least the extending parts of the back layer are self-adhesive and that thus the device is fixed on the substrate (FIG. 8).

Solid substrates with which the gel film may interact and the possible interactions may be of various nature. For instance, the interaction of the gel film and solid substrates may be that the gel film is used as adhesive for anchoring devices on solid surfaces.

In a preferred embodiment, the substrate with which the gel film interacts is damaged skin.

The composition of the gel film which interacts with damaged skin, as e.g. burns, scalds, acid burns, surgical wounds, bedsores, ulcers of the leg, or as well in the case of trivial injuries, such as grazes and scratch marks, is chosen in such a way that all components exhibit optimum compatibility with tissues in order to increase the natural healing processes of the wounds instead of hindering or interrupting them. The cationic polymer component preferably is type-A-gelatin, since gelatin is known for long in the use for wound treatment as absorption polymer having a blood-staunching effect. For this use preferably sodium carboxymethylcellulose or low esterified pectines are used as anionic components. The device creating or enabling the interaction between gel film and damaged tissue preferably is transparent, so that the damaged tissue may be observed without the necessity to remove the device.

The adjustment of the absorption capacity for wound exudates and absorption kinetics of the gel film is of special importance. For instance, the basic polymers type-A-gelatin and sodium carboxymethylcellulose exhibit a rapid and high absorption and swelling capacity when combined with each other. Thus, the course and extent of the absorption must be influenced by incorporating further additives, whereby the content of additional additives must be chosen in such a way that the adhesion and thus the handling of the gel film in swollen condition is not affected.

Polymers which are physiologically acceptable are preferably used. These polymers have been used in other form in the treatment of wounds for long, e.g. polyvinyl pyrrolidone, polyvinyl alcohol, and especially collagen.

By the use of the polymers mentioned, it is achieved that the absorption behaviour of the gel film can be controlled in such a way that great amounts of liquid can be absorbed and stored over a predetermined period of time and within a predetermined velocity, without drying up the wound. It is of special advantage to incorporate collagen into the gel film, since the collagen is removed from the gel film during use and thus is available as an active principle in the wound for the promotion of wound healing.

A further possibility to control the absorption behaviour and capacity is to give the gel film a porous structure by purposive foaming of the mass prior to spreading. Due to the hollow spaces in the gel film after drying, the storage capacity for wound exudate is increased, and the absorption velocity is increased by the fine capillares which run through the gel film.

It is possible, too, to construct the gel film as multilayered structure, and to adjust the desired characteristics by combining various homogeneous layers of different composition, or by combining homogeneous and porous layers.

If the gel film is provided with a back layer, this back layer may be permeable to water vapour in a special embodiment, so that the liquid taken up by the wound, which reaches the backward boundery of the wound dressing due to diffusion transport in the gel film, is released to the environment via the back layer, so that no liquid accumulation occurs on the wound, which would hinder the course of wound healing.

If the transparence of the device, which brings into contact the gel film with the damaged tissue, is of minor importance, the gel film may be built up to a multi-layer composite by means of foams, such as, e.g. polyurethane foams or textile fabrics. If the adhesion of the device on the substrate is effected by the gel film itself in this use, preferably sugar, honey, panthenol, or natural resins and gums, such as, e.g. mastic, gum arabic or karaya gum are employed as tackifiers.

In another preferred embodiment, the substrate with which the gel film interacts is intact skin. The gel film may, e.g. be part of the devices which are used in cosmetics as masks or films for the treatment, e.g. of aged skin, wrinkles, blemished skin, as toilet article, for removal of hair, for reduction of sweating, or as protection against light.

A preferred interaction between gel film and intact skin is the dermal, intradermal, or transdermal release of active substance.

For the dermal treatment of local skin diseases the following substances are employed: local anesthetics, local antibiotics, antimycotics, antihistamines, and itching reducing drugs, keralolytics, and caustic pharmaceuticals, antiscabies agents, steroids, and various substances for the treatment of acne, psoriasis, or light dermatosis.

Active substances being applied intradermally are, steoridal and non-steoridal antirheumatics, antiphlogistics, bloodstream stimulating substances, or vasoprotectors and vasoconstrictors for the treatment of vascular diseases. Transdermally applicable active substances are, e.g. neuroleptics, antidepressants, tranquilizers, hypnotics, pychostimulants, analgesics, muscle relaxants, anti-Parkinson agents, ganglion blocking agents, sympathomimetics, alpha-adrenergic blockers, beta-adrenergic blockers, antisympathotonics, antidiabetic agents, therapeutical agents for corona diseases, hypertensors, antiasthmatics, or diuretics.

It is known that the permeability of the skin for active substances depends, amongst others, on the thickness, the content of lipides, and the water content of the scrafskin. It is known as well that the increase of the water content of the scrafskin results in a swelling which increases the permeability of the skin for many active substances by the factor 4–5. This swelling of the scrafskin can be achieved by applying the gel film according to the present invention by the release of water from the gel film to the skin.

The functions, which can be satisfied by the gel film in this use, are many-fold. In the simplest case a device for release of active substance to the skin consists of a back layer being impermeable for active substances, a reservoir for substances, and a protective layer which is removed prior to application (FIG. 1).

If the gel film is used as single-layer substance reservoir, the release of active substance and the hydration of the skin by means of added water depend on the thickness of the film, the content of active substance in the gel film, and the thermodynamic activity of active substance in the gel film, whereby there are various possibilities to change the thermodynamic activity in the gel film, in dependence of the properties of the substance.

For instance, if the solubility of active substance is dependent on the pH, the solubility may be increased or decreased by incorporating pH-regulators, such as buffer systems, and thus the release may be regulated. Many active substances are of basic character and have at neutral pH the lowest solubility due to reduced ionisation. In this case, the solubility can be increased by adding acid additives. It is possible, too, to reduce the solubility in the case of active substances being highly soluble in water, and whose release from hydrophilic matrices is principally retarded, by the selection of the gel film composition, adjustment of the pH-value, and reduction of the water content.

A further possibility to influence the thermodynamic activity and thus the regulation of release, e.g., if extremely lipophilic active substances are used, is to provide the gel film with a lipophilic inner phase.

This film then practically is a mechanically stable, film-like cream.

The composition of the inner phase, particularly the composition of a possibly necessary emulsion stabilizing component, is chosen in such a way that a high affinity towards the skin lipides is given. In this it is achieved that on contact with the skin, the lipide vesicles are opened by destabilization of the emulsion, and incorporated substance is released to the skin.

A further advantageous effect of the gel film is that it might be activated by application, i.e. that by warming up the gel film to body temperature the thermodynamic activity of the active substance, or of the lipophilic inner phase, can be increased, when the composition is adequate.

The release unit of a device for the dermal, intradermal, or transdermal application not necessarily is a single-layer reservoir, but it might also be multi-part. For instance, several gel films containing active substances may be connected to a laminate (FIG. 2). The possibilties for controlling, e.g. are different composition of the individual layers, or different loads with active substance.

In a multi-layer composite a gel film which is free of active substance can, e.g. serve as barrier between lipophilic layers, said barrier only becoming permeable on warming up to body temperature (FIG. 3); or it might serve as barrier between lipophilic reservoir and skin, thus being a control membrane for the release of active substance (FIG. 4). It is possible too, that the gel film or a gel film composite is a carrier of active substance, and a lipophilic layer free of active substance serves as control membrane between gel reservoir and skin (FIG. 5), whereby the lipophilic layer, if it is rendered self-adhesive, also serves to anchor the gel film on the skin. In another embodiment the gel film is in the form of sheets and at least partially surrounded by lipophilic polymer film, or itself surrounds at least partially a lipophilic element. Hydrophilic and lipophilic part of the device may contact the skin in this case (FIG. 6). If both parts contain the same active substance or substances, one part of the device can release active substance to the skin in an extremely rapid manner as initial dose for the rapid achievement of a therapeutically effective blood level due to the extremely different chemical nature.

The other part of the device delivers with retardation the dosage necessary to maintain the blood level over a longer period of time.

However, the different parts of the device may contain different active substances. In the case of diseases which are usually treated with a combination of active substances, the dermal, intradermal, or transdermal application of these combination frequently is not possible, since, e.g. pharmacokinetics and pharmacodynamics of the active substances are extremely differing from each other when applied to the skin; the active substances may not be stored in one reservoir due to chemical differences; or at least one active substance does not exhibit the necessary release. The combination of a hydrophilic gel film with an emulsion gel film or with a conventional lipophilic polymer film, which each contain a different active substance, makes possible that a specific formulation can be chosen for each active substance, said formulation giving the desired release. The advantage of this embodiment is that the combination therapy with various medicines does not necessarily require the application of various devices. Furthermore, it is possible by combining the gel film with more lipophilic films, to release different active substances at different points of time. An active substance can be released very rapidly from one part of the device, and achieves rapid therapeutically effective blood levels which, after a certain period of time, preferably after 4–12 hours, are reduced again.

The other part of the device is a retardation formulation which with retarded release slowly releases another active substance to the skin so that the therapeutically necessary concentration is achieved not before some time has passed, preferably after 4–12 hours. By this way of alternating release of active substances, it is possible, e.g. to consider more purposeful specific therapy schemes, which is usual in the peroral application of medicines, but without the disadavantages of peroral medicines. For instance, by the alternating release of nitrates and calcium antagonists, or nitrates and beta-receptor blockers an effective angina pectoris prophylaxis can be carried out, without creating a tolerance against nitrates. In all these cases it has to be safeguarded by the selection of the formulations, or by additional barrier layers that no changes of the release behaviour during storage occur due to interactions between hydrophilic and lipophilic parts of the device.

In another embodiment, the gel film surrounds a lipophilic active substance store or reservoir, or the gel film is an active substance store or reservoir in a lipophilic film (FIG. 7). In both cases, the active substance reservoir does not directly contact the skin; its function is the controlled release of active substance to the surrounding film over a long period of time. During storage an equilibrium of active substance of storing element and surrounding element appears; the equilibrium being dependent on the saturation solubility of the active substance in the surrounding film. After application the active substance penetrates from the surrounding element into the skin. Depending on the diffusion velocity of the active substance from the reservoir into the surrounding element, the diffusion velocity of the active substance in the surrounding element and the penetration rate into the skin, active substance is continuously delivered from the reservoir over a long period of time, until the saturation solubility of the active substance in the reservoir is fallen below.

According to a further preferred embodiment, the substrate with which the gel film interacts is mucous membrane.

The gel film serves as carrier for locally or systemically effective substances for the release to mucous membranes, such as mucosa of the eye, the mouth, and the nose, rectal, vaginal, or uterinal mucous membranes. The adhesion on the mucous membranes, generally called bioadhesion, is effected by interfacial forces between the musous membrane and the gel film, through which the film is connected with the tissue over a pre-determined period of time. Polymers are added to the gel mass prior to the production of the film, said polymers are known to have a high affinity towards mucous membranes and to show an excellent adhesion over a long period of time, such as, e.g. carboxymethylcellulose, polyacrylic acid (Carbopol® of Goodrich), tragacanth, sodium alginate, hydroxyethyl cellulose, hydroxypropyl cellulose or karaya gum. After application, the gel film absorbs body secretions, swells and releases active substance over a longer period of time. The release is either effected by erosion of the gel film, or by controlled decay of the gel structure, or by a mixture of both mechanisms. Special purposes are, e.g. occular application of pilocarpine, or local antibiotics, and, e.g. in the case of vaginal or intrauterine application, the long-term release of estrogens and/or gestagens in the contraception.

In the case of buccal or sublingual application of the gel film, active substance can be released to the system circulation via the mucous membrane of the mouth, on the one hand. In this case the gel film has a back layer which prevents that larger amounts of active substance are removed from the gel film via the saliva and are resorbed gastrointestinally after choking.

On the other hand, via the buccal application of the gel film, e.g. fluorides for the caries prophylaxis or active substances for the treatment of diseases, such as, inflammations in the mouth and throat region, are released. The following substances are used, for example, local antiseptics such as chlorohexidine, benzalkonium, hexetidine, dequalinium chloride, acriflavinium, or ethacridine; local anesthetics, such as benzocaine or lidocaine; local antibiotics, such as gramicidin or tyrothricine; adstringents, such as, e.g. aluminium salts or plant extracts from sage, myrrh or benzoe.

The substrate with which the gel film interacts can as well be the surface of a plant. So, for instance, superficial, locally limited plant diseases can be treated with active substances which are released from the gel film to the plants' surfaces. Furthermore, active substances with systemic effectivity, which serve the protection of the plant against agents of diseases and parasites, or the treatment of plants after infection and already excisting infestation with pests, the growth regulation and the nutrition of the plant, can be released from the gel film to the plants' surfaces, such as, e.g. to the leafs, the stem, or the roots. After release from the gel film the active substance penetrates into the epidermal and subepidermal tissues of the plant, enters transport system of the plant, and is distributed in the plant systemically after resorption.

The systemic active substances may, e.g. be fungicides, such as bitertanole, fenarimole, triforine, aluminiumfosetyl, or tridemorph; insecticides, such as nicotine, demeton, dimethoate, fenthion, or menazon; or plant hormones, such as auxins, gibberellins, cytokinins, or abscisic acid. However, the gel film can also serve as preservation of isolated parts of the plant, e.g. by wrapping the parts of the plant, or may serve as supply for cut flowers with nutrients and water by wrapping the cuts.

The interactions between gel film and liquid substrate may as well be very many-fold. The gel film may, e.g. be part of a device which serves as bathing additive. After removal of the protective layer and/or back layer, and introducing the device into the bath, the following substances may be released from the gel film to the liquid substrate, e.g. odorous substances, dyes, cleaning agents, toiletries, agents for the treatment of skin malfunctioning, itching reducing agents, such as camomile, sulphur, pollard, or milk protein; agents having a stimulating effect, such as lavender, rosemary, or oxygen releasing compounds; agents having a calmative effect, such as extracts or components of valerian, hops, or melissa; active substances for the relief of rheumatic complaints, such as salicylic acid and salicylic acid ester, nicotinates; extracts and components of arnica, calendula, or capsicum; or active substances for the relief of complaints in connection with colds, such as extracts and components of eucalyptus, spruce needle, dwarf pine needle, or thyme.

The gel film can also be part of devices which are introduced into aquariums, and in which the interaction between gel film and liquid substrate, e.g. is the release of active substances for the prevention and treatment of fish diseases, or for combatting the growth of algas.

Devices for creating interactions between a gel film and a gaseous substrate usually have impermeable back and protective layers. The gel film preferably contains active substances which are volatile at room temperature, and which are released to the gaseous substrate after removal of the protective layer and/or back layer. In order to regulate the active substance release there can be arranged porous membranes between back layer and gel film, and/or between protective layer and gel film.

A possible use for such a device, for example, is the treatment of colds with a gel film containing essential oils, such as, e.g. anise oil, fennel oil, eucalyptus oil, thyme oil, camomile oil, peppermint oil, camphor, oil of turpentine, dwarf pine needle oil; or individual volatile components of essential oils, such as, e.g. menthol, eucalyptol, or phellandrene. For instance, the gel film can be put on the pillow prior to falling asleep after removal of the back layer thus releasing the discharge surface, so that during the night volatile active substance is released and inhaled. However, the gel film may as well have an adhesive fixation element (FIG. 11, 12) and is applied, after removal of the back layer and protective layer, onto the skin in the upper chest region. By warming up to body temperature, the release of the volatile active substance is increased as is the amount inhaled. The advantage towards commercial gels, balsams, and liniments is that the device enables a controlled release of substance over a longer period of time, and that sticking with clothes or bed linen is prevented. According to another embodiment, the gel film comprises calmative or sleep promoting volatile active substances, such as, e.g. components or extracts of melissa, hops or valerian. The application is carried out as described above. The interaction between gel film and gaseous substrate may as well be such that volatile active substances for the protection against mosquitos, houseflies, horseflies, or wasps are released from the gel film into the air. Such active substances can be insecticides, such as, e.g. pyrethrines, synthetic pyrethroids, or propoxur; or repellents, such as, e.g. diethyltoluamide, dimethylphthalate, laurel oil, eucalyptus oil or anise oil.

EXAMPLES 1–18

In a vessel which can be closed tightly the solutizer (ammonium hydroxide in examples 1–12, glacial acetic acid in examples 13-18) is added to the solvent which is water (examples 1–8, 13–18) or to the solvent mixture water/ethanol (examples 9–12), and the mixture is heated to 65° C. Anionic polymer, cationic polymer and the other formulation components are added one after the other, and after each addition it is stirred and homogenized in the closed vessel until the respective substance is solved clearly. The mass is stirred until a temperature of approximately 45° C. (examples 1–11, 13–18) is reached and spread or coated onto a carrier, which may be the back layer, the protective layer, or an intermediate cover, at this temperature up to the desired thickness of the layer; then it is dried in the drying channel at 80° C. to a residual moisture of approximately 25%.

The manufacturing process of example 12 differs in such a way that in all steps up to the drying a temperature of 30° C. is not exceeded, and the mass is dried after brushing at 60° C.

The gel films so obtained are swellable in water, but are insoluble. All films are completely transparent in dry condition. Some films exhibit in swollen condition slight to moderate cloudiness and/or have a grained surface (examples 4, 8, 9, 12). In examples 2, 4, and 6 the mass exhibits a very high viscosity prior to the production of the film, which leads to the fact that during the coating irregularities in the brushed surface and thus variations of the area weight of the dried film occur. The formulations according to examples 1, 5, 7, 10, 11, and 16 are best to handle in the production of the mass, they allow to incorporate sufficient further auxiliaries and/or active substances, and deliver transparent, homogeneous films with a high solidity in both dried and swollen condition.

|  | Example | | | | | | | | |
|---|---|---|---|---|---|---|---|---|---|
|  | 1 | 2 | 3 | 4 | 5 | 6 | 7 | 8 | 9 |
| Type-A-gelatin | 10 | 10 | 10 |  |  |  |  |  | 15 |
| Jaguar C 17 S$^R$ |  |  |  | 2 | 2 | 2 |  |  |  |
| Eudragit E 100$^R$ |  |  |  |  |  |  | 10 | 10 |  |
| Na-CMC Tylose C 10000$^R$ | 3 |  |  |  | 2 |  |  | 2 |  |
| Na-CMC Tylose C 1000$^R$ | 1 |  |  |  |  |  |  |  |  |
| HPMCP HP 55$^R$ |  |  |  |  |  |  |  |  | 5 |
| Jaguar CMHP$^R$ |  |  |  |  |  |  |  | 1 |  |
| Meyprofilm 122$^R$ |  |  |  |  | 1 |  |  |  |  |
| Meypro-Gum R 740$^R$ |  |  |  | 2.5 |  |  |  |  |  |
| NV-Pectin |  |  | 2 |  |  | 2 |  | 2 |  |
| Pectic acid |  |  |  |  |  | 1 |  |  |  |
| Xanthene, Keltrol F$^R$ |  | 1 |  |  |  | 1 |  |  |  |
| Eudragit S 100$^R$ |  |  | 4 |  |  |  |  |  |  |
| Carboset 525$^R$ |  |  |  |  |  |  | 10 |  | 10 |
| Aquakeep 10 SH$^R$ |  |  |  |  |  |  |  | 1 |  |
| Glycerol | 2 |  |  |  |  |  | 5 |  | 5 |
| Propylene glycol |  | 0.5 | 0.5 | 0.5 | 0.5 | 0.5 |  | 4 |  |
| Triethylcitrate |  |  |  |  |  |  |  |  |  |
| PVA Mowiol 10-98$^R$ |  |  | 1 |  | 2 | 2 | 3 |  |  |
| PVP Kollidon 30$^R$ |  | 4 |  |  |  | 1 |  |  | 5 |
| PVP Kollidon 90$^R$ |  |  |  |  |  |  | 2 | 2 |  |
| HPC Klucel LF$^R$ |  |  |  |  |  |  |  |  |  |
| Collagen paste (20% in water) |  | 2 |  |  | 2 |  |  | 2 |  |
| Phenylethanol | 0.5 | 0.5 | 0.5 | 0.5 | 0.5 | 0.5 | 0.5 | 0.5 |  |
| Cetylpyridinium chloride | 0.05 | 0.05 | 0.05 | 0.05 | 0.05 | 0.05 | 0.05 | 0.05 |  |
| Ammonium hydroxide 28% |  | 2.5 | 2.5 | 2.5 | 2.5 | 2.5 | 2.5 | 2.5 | 2.5 |
| Glacial acetic acid |  |  |  |  |  |  |  |  |  |
| Ethanol |  |  |  |  |  |  |  |  | 25 |
| Water | 80.95 | 79.45 | 79.45 | 91.95 | 87.45 | 87.45 | 66.95 | 72.95 | 32.5 |

|  | Example | | | | | | | | |
|---|---|---|---|---|---|---|---|---|---|
|  | 10 | 11 | 12 | 13 | 14 | 15 | 16 | 17 | 18 |
| Type-A-gelatin | 15 | 15 |  | 10 | 10 | 10 |  |  |  |
| Jaguar C 17 S$^R$ |  |  |  |  |  |  | 1 | 2 |  |
| Eudragit E 100$^R$ |  |  | 7.5 |  |  |  |  |  | 10 |
| Na-CMC Tylose C 10000$^R$ | 2.5 |  |  |  |  |  |  |  |  |
| Na-CMC Tylose C 1000$^R$ |  |  |  |  |  |  |  |  |  |
| HPMCP HP 55$^R$ |  |  |  |  |  |  |  |  |  |
| Jaguar CMHP$^R$ |  |  |  | 2 |  |  |  | 2 |  |
| Meyprofilm 122$^R$ |  |  |  |  | 1 |  | 3 |  |  |
| Meypro-Gum R 740$^R$ |  |  |  |  | 2.5 |  |  |  | 2.5 |
| NV-Pectin |  |  |  |  |  |  |  |  |  |
| Pectic acid |  |  |  |  |  | 5 |  |  |  |
| Xanthene, Keltrol F$^R$ |  |  |  |  |  |  |  |  |  |
| Eudragit S 100$^R$ |  |  | 7.5 |  |  |  |  |  |  |
| Carboset 525$^R$ | 7.5 | 10 |  |  |  |  |  |  |  |
| Aquakeep 10 SH$^R$ |  | 1 |  |  |  |  |  |  |  |
| Glycerol |  |  |  | 3 | 3 | 3 | 0.5 | 0.5 | 2.5 |
| Propylene glycol | 2.5 |  | 1.5 |  |  |  |  |  |  |
| Triethylcitrate |  | 3 |  |  |  |  |  |  |  |
| PVA Mowiol 10-98$^R$ |  |  |  |  |  |  |  |  |  |
| PVP Kollidon 30$^R$ | 2.5 |  | 1.5 |  |  |  |  |  |  |
| PVP Kollidon 90$^R$ |  |  |  |  |  |  |  |  |  |
| HPC Klucel LF$^R$ |  |  | 2 |  |  |  |  |  |  |
| Collagen paste (20% in water) | 2.5 |  |  |  |  |  |  |  |  |
| Phenylethanol | 0.5 | 0.1 |  | 0.5 | 0.5 | 0.5 | 0.1 | 0.1 | 0.5 |
| Cetylpyridinium chloride |  | 0.05 |  |  |  |  |  |  |  |
| Ammonium hydroxide 28% | 2.5 | 2.5 | 2.5 |  |  |  |  |  |  |
| Glacial acetic acid |  |  |  | 1 | 1 | 1 | 1 | 1 | 1 |
| Ethanol | 20 | 34 | 40 |  |  |  |  |  |  |
| Water | 44.5 | 34.35 | 37.5 | 83.5 | 83 | 80.5 | 94.4 | 94.4 | 83.5 |

All numerical data is stated in %-wt

EXAMPLE 19

20 g phenylethanol, 0.04 g cetylpyridinium chloride and 2.5 ml ammonium hydroxide 28% are added to 235 ml deionized water having a low content of germs. The mixture is heated to appr. 65° C. 30.0 g glycerol, 13.0 g polyvinylalcohol (Mowiol 28-99®), 35.0 g polyvinyl pyrrolidone (Kollidon 30®), 75.0 g type-A-gelatin, 15.0 g Na-carboxymethylcellulose C 10000 (Tylose®), 2.5 g Na-carboxymethylcellulose C 1000 (Tylose®), 35.0 g saccharose, 50.0 g medical honey, and 35.0 g panthenol are added one after the other. In the closed vessel it is stirred and homogenized after each addition until the added substance is solved clearly. Subsequently the mass is stirred until a temperature of 45° C. is reached, and 20.0 g collagen paste (20% in water) are stirred in. The mass is stirred under vacuum until there are no air bubbles left and is spread on a 40 µm-polyurethane film at a temperature of 45° C. and an area weight of 2340 g/m$^2$. In the drying channel at a temperature of 80° C. it is then dried to a residual moisture of appr. 25%, corresponding to an area weight of 1680 g/m$^2$. After drying, the film is covered with a siliconized foil, punched to size and made-up. The gel film is transparent, adheres to the skin and can be used as dressing for wounds with high exudation, due to its high fluid absorption capacity.

EXAMPLE 20

0.45 g phenylethanol, 0.01 g cetylpyridinium chloride and 1.0 ml ammonium hydroxide 28% are added to 100 ml deionized water poor of germs. The mixture is heated to appr. 65° C.

One after the other, 7.0 g glycerol, 10.0 g Carboset 525®, 20.0 g type-A-gelatin, 7.0 g polyvinyl pyrrolidone (Kollidon 30®), 5.0 g saccharose, 10.0 g medical honey, and 7.0 g panthenol are added. In the closed vessel it is stirred and homogenized after each addition until the added substance is solved clearly. The mass is stirred until a temperature of 50° C. is reached, and 10.0 g collagen paste (20% in water) is stirred in. The mass is brushed on a 40 µm-polyurethane film at a temperature of 50° C. and an area weight of 775 g/m$^2$. In the drying channel, at a temperature of 80° C., it is then dried to a residual moisture of appr. 25%, corresponding to an area weight of 400 g/m$^2$. After drying, the film is covered with a siliconized foil, punched to format and finished. The gel film is transparent, adheres to the skin, and can, e.g. be used as dressing for wounds with low exudate or for trivial wounds.

EXAMPLE 21

20.0 g ethanol, 0.25 g phenylethanol, 0.005 g cetylpyridinium chloride, and 1.0 ml ammonium hydroxide 28% are added to 34.245 ml deionized water poor of germs. The mixture is heated to appr. 45° C. One after the other, 5.0 g hydroxypropyl cellulose (Klucel LF®), 3.0 g Na-carboxymethylcellulose C 10000 (Tylose®), 1.0 g Na-carboxymethylcellulose C 1000 (Tylose®), 3.0 g glycerol, 25.0 g type-A-gelatin, 2.5 g collagen paste (20% in water), 2.5 g myrrh tincture, and 2.5 g sage tincture are added in clearly solved condition. The mass is spread on a siliconized polyester foil at a temperature of 45° C. and an area weight of 300 g/m$^2$. In the drying channel at a temperature of 60° C., it is then dried to a residual moisture of appr. 25%, corresponding to an area weight of 150 g/m$^2$. After drying, the film is covered with a siliconized foil, punched to size and finished. The gel film is applied on the mucous membrane of the mouth, adheres to it, and releases the active substances during wetting and swelling, which serves to treat inflammations within the mouth and throat region.

EXAMPLE 22

5.0 g phenylethanol, 1.0 ml ammonium hydroxide 28%, 7.0 g Eudragit E 100 ®, 7.0 g Carboset 525®, 3.5 g propylene glycol, and 5.0 g Kollidon 30® are added to 36.0 ml ethanol and 16.0 g deionized water having a low content of germs. It is stirred and homogenized until the added substances are clearly solved. The solution is slowly stirred in in portions into a mixture of 32.0 g Acronal V 205®, 17.0 g Acronal 85 D®, and 1.0 g ammonium hydroxide 28%. The mass is spread on a 40 µm-polyurethane film at room temperature and an area weight of 375 g/m$^2$. In the drying channel at a temperature of 60° C., it is then dried to a residual moisture of appr. 5%, corresponding to an area weight of appr. 150 g/m$^2$. After drying, the film is covered with a siliconized foil, punched to format and made-up. The gel film can be used as contact adhesive for medical articles and exhibits good adhesion and cohesion even on sweaty skin.

EXAMPLE 23

0.5 g phenylethanol and 1.0 ml ammonium hydroxide 28% are added to 44.0 ml deionized water having a low content of germs. The mixture is heated to appr. 65° C. One after the other, 2.0 Mowiol 10–98®, 0.5 g glycerol, 2.0 g Tylose C 1000®, 5.0 g Carboset 525®, and 10.0 g type-A-gelatin are added. In the closed vessel it is stirred and homogenized after each addition until the added substance is clearly solved. The mass is stirred until a temperature of 50° C. is reached, and 2.5 g collagen paste (20% in water) is stirred in. The mass is maintained at this temperature (waterphase).

10.0 g arnica oil, 6.0 g camphor, 4.0 g polyethylene glycerole monostearate, and 8.0 g cetylstearyl alcohol are heated to 50° C. and are slowly stirred until a clear solution results (oil-phase). The water-phase is incorporated into the oil-phase in portions at a temperature of 50° C. under stirring and homogenizing. The homogeneous cream coloured mass is brushed on a 30 µm-polyester foil at a temperature of 50° C., and an area weight of 600 g/m$^2$. In the drying channel at 50° C. it is dried to a residual water content of appr. 25%, corresponding to an area weight of 410 g/m$^2$. After drying, the film is covered with a siliconized foil, punched to size and finished (acc. to FIG. 8). The gel film can be used for the topical bloodstream stimulation, and as inhibitor for inflammations, e.g. in the case of slight rheumatic complaints or sports injuries.

EXAMPLE 24

0.5 g phenylethanol and 1.0 ml ammonium hydroxide 28% are added to 41.0 ml deionized water having poor of germs. The mixture is heated to appr. 65° C. One after the other, 2.0 g HPMCP HP 55®, 3.0 g Eudragit S 100®, 2.0 g Carboset 525®, 2.0 g Kollidon 30®, 2.0 g propylene glycol, 5.0 g type-A-gelatin, and 2.5 g collagen paste (20% in water) are added. When all components are solved clearly, the solution is cooled to appr. 45° C. and added under slow stirring in portions to 40.0 g Acronal V 205® (water-phase).

6.0 g Tween 20, 9.0 g Tween 61, 8.0 g eucalyptus oil, 10.0 g dwarf pine needle oil, and 2.0 g anise oil are mixed with one another at room temperature and are homogenized (oil-phase).

The warm water-phase is incorporated under stirring and homogenization in portions into the oil-phase. The mass having an area weight of appr. 680 g/m$^2$ is then spread on a porous 15 μm-polyester foil, and is dried in the drying channel at a temperature of 45° C. to a residual water content of appr. 10%, corresponding to an area weight of 400 g/m$^2$. After drying, the film is covered with a siliconized foil, punched to size and made-up (acc. to FIG. 12). The gel film can be stuck on the skin in the upper region of the chest in the case of colds, and slowly releases the essential oils for inhalation after removal of the backward cover on warming up to body temperature.

BRIEF DESCRIPTION OF THE DRAWINGS

In the following, FIGS. 1 to 12 illustrating the invention are explained:

FIG. 8a and 8b show devices in which a gel film (1) is covered with a protective layer (3) and a back layer (2) having larger area dimensions than the gel film (1) and being coated completely (FIG. 8a) or partially (FIG. 8b) with an adhesive film (5).

FIG. 9, 10a and 10b show embodiments of a gel film (1) having an adhesive layer (5), whereby this adhesive layer covers the gel film discontinuously, i.e., broken, either completely (FIG. 10a) or partially (FIG. 10b).

In FIG. 11a and 11b a gel film (1) is shown which is combined with an control element (6) which is a broken layer and is connected with the back layer (2) via an adhesive layer (5) (FIG. 11a). In FIG. 11b a second adhesive layer (5') is positioned between gel film (1) and protective layer (3), said adhesive layer serves to anchor the gel film (1) onto a desired surface after removal of the protective layer (3).

In FIG. 12 a device is shown in which the gel film (1) is covered with a porous control membrane (6) on its back side, said membrane having larger area dimensions than the gel film (1) and the extending parts of which are covered with an adhesive layer (5'). The porous area of control membrane (6) is covered with a back layer (2) which is covered with an adhesive film (5). The back layer (2) is of larger area dimension than the porous area of the control membrane (6), e.g., in the form of an extending flap so that the back layer (2) with the adhesive film (5) can easily be removed prior to use.

Figure 1:
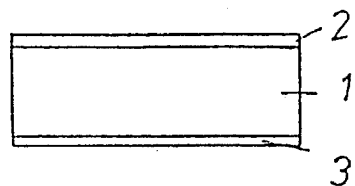
FIG. 1 shows a gel film (1) which is provided on one side with an impermeable back layer (2) and on the opposite side with a removable impermeable protective layer (3).
Figure 2:
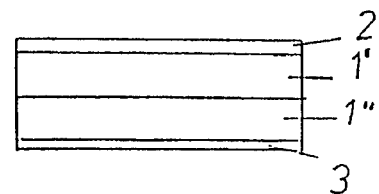
FIG. 2 describes a multi-layer gel film (laminate) in which the gel film (1) is divided into two layers (1', 1").
Figure 3:
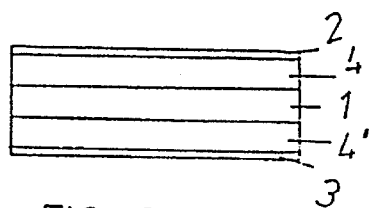
FIG. 3, as well, shows a multi-layer composite in which a gel film (1), which is free of substance or active substance, respectively, is surrounded sandwichlike by two lipophilic polymer films (4, 4') which both contain substance or active substance, respectively. This arrangement again is covered by the back layer (2) and protective layer (3).
Figure 4:
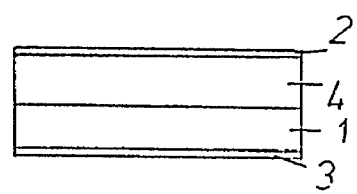
In FIG. 4 a gel film (1), which is free of substance or active substance, respectively, is shown which is covered on one side by the protective layer (3), and which serves as control membrane for the substance or active substance containing polymer film (4), which is covered with the back layer (2).
Figure 5:
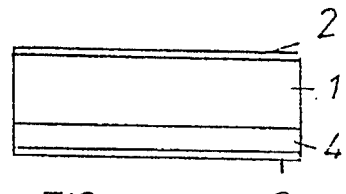
In FIG. 5 the active substance containing gel film (1) is combined on the side facing the substrate with a lipophilic polymer film (4) which is free of active substance and serves as control membrane.
Figure 6:
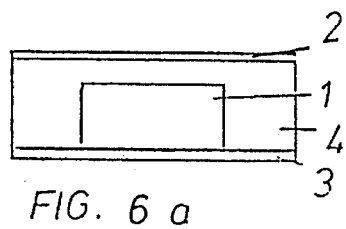
FIG. 6a and 6b show an embodiment of the gel film (1) in which the gel film is surrounded at least partially by the lipophilic polymer film (4), or in which the film itself at least partially surrounds a lipophilic element. Both elements may contain active substance.
Figure 6:
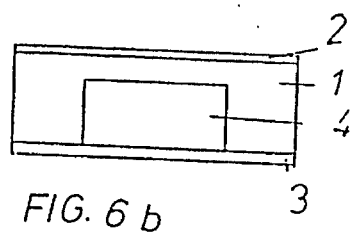
Figure 7:
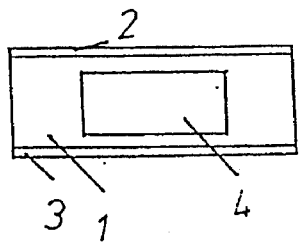
FIG. 7a shows a further embodiment in which the gel film (1) acting as control membrane encloses a lipophilic active substance reservoir (4)
in FIG. 7b the gel film (1) acting as storing element is completely embedded into a lipophilic film (4) acting as control element. The lipophilic storing element (4) and the gel film (1) acting as storage, respectively, may directly border to the back layer (2) with one surface (FIG. 7c and 7d).
Figure 7:
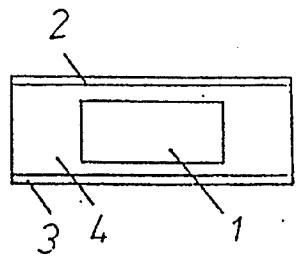

We claim:

1. A mechanically stable, flexible, hydrophilic, water-swellable but insoluble gel film sheet having a weight of about 150 to 2340 grams per square meter and consisting of
   (a) 0.5 to 30%-wt of at least one water-soluble polymer being anion-active at neutral pH comprising carboxymethyl cellulose
   (b) 0.5 to 50%-wt of at least one water-soluble polymer being cation-active at neutral pH comprising type A gelatin
   (c) 0.1 to 20%-wt of at least one moisturizer comprising glycerol and
   (d) 0.1 to 70%-wt of water
   (e) 0 to 75%-wt of water-soluble or water-dispersible auxiliaries
   (f) 0 to 50%-wt of active substance.

2. A gel film according to claim 1, characterized in that it contains as water-soluble or water-dispersible auxiliaries (e) at least one of softeners, thickeners, penetration accelerators, tackifiers, preserving agents, disinfectants, pH-regulators, antioxidants, emulsion stabilizers, cross-linking agents, fillers and/or foam stabilizers.

3. A gel film according to claim 2, characterized in that it contains collagen as thickening agent.

4. A gel film according to claim 2, characterized in that it contains as tackifiers natural, semi-synthetic and/or synthetic resins or gums.

5. A gel film according to claim 2, characterized in that it contains as tackifiers honey, sugar and/or panthenol.

6. A gel film according to claim 1, characterized in that it contains a lipophilic inner phase.

7. A gel film according to claim 1, characterized in that it is transparent.

8. A gel film according to claim 1, characterized in that it has a porous structure.

9. A gel film according to claim 1, characterized in that it is has a multi-layered structure.

10. A gel film according to claim 1, characterized in that it is biologically decomposable.

* * * * *

UNITED STATES PATENT AND TRADEMARK OFFICE
CERTIFICATE OF CORRECTION

PATENT NO. : 5,456,745

DATED : October 10, 1995

INVENTOR(S) : Roreger, et al.

It is certified that error appears in the above-identified patent and that said Letters Patent is hereby corrected as shown below:

Col. 18, line 43    Delete " /or "

Col. 18, line 59    Delete " is "

Signed and Sealed this

Sixteenth Day of April, 1996

BRUCE LEHMAN

*Attest:*

*Attesting Officer*      *Commissioner of Patents and Trademarks*